(12) United States Patent
Hagemann

(10) Patent No.: US 7,179,086 B2
(45) Date of Patent: Feb. 20, 2007

(54) ROOT CANAL INSTRUMENT SET

(75) Inventor: Frank Hagemann, Lemgo (DE)

(73) Assignee: Gebr. Brasseler GmbH & Co. KG, Lemgo (DE)

( * ) Notice: Subject to any disclaimer, the term of this patent is extended or adjusted under 35 U.S.C. 154(b) by 0 days.

(21) Appl. No.: 11/126,949

(22) Filed: May 10, 2005

(65) Prior Publication Data
US 2005/0282109 A1 Dec. 22, 2005

(51) Int. Cl.
A61C 5/02 (2006.01)
(52) U.S. Cl. ...................................... 433/102
(58) Field of Classification Search ................ 433/102, 433/81, 224
See application file for complete search history.

(56) References Cited

U.S. PATENT DOCUMENTS 5,752,825 A 5/1998 Buchanan et al.
6,012,921 A 1/2000 Riitano et al.
6,520,774 B1* 2/2003 Mays .......................... 433/102
2003/0013067 A1 1/2003 Bleiweiss et al.
2004/0229188 A1* 11/2004 Lewis et al. ................. 433/102

FOREIGN PATENT DOCUMENTS

| DE | 10135820 | 1/2003 |
|----|----------|--------|
| EP | 1354566 | 10/2003 |
| WO | 2004/091422 | 10/2004 |

OTHER PUBLICATIONS

European Search Report dated Sep. 5, 2005 for related European Application No. 05004559.0.

* cited by examiner

*Primary Examiner*—Cary E. O'Connor
(74) *Attorney, Agent, or Firm*—Sheridan Ross P.C.

(57) ABSTRACT

Root canal instrument sets and instruments having high loadability and high breakage safety.

8 Claims, 3 Drawing Sheets

ROOT CANAL INSTRUMENT SET

The present invention relates to a root canal instrument set comprising at least two root canal instruments according to the preamble of the main claim.

The prior art discloses very different configurations of root canal instruments provided in sets. Hence, the dentist can treat a root canal by using the individual root canal instruments in sequence. The root canal is thus treated in steps.

The prior art basically shows two different types of root canal instrument sets. In the one type, the first tool is relatively thin, whereas the subsequent tool has a respectively larger diameter. The root canal is thus enlarged in its diameter in steps. The other procedure, which is also called "crown-down preparation", starts with a large-diameter instrument by which the upper outer region of the root canal is treated. The subsequent instrument has a smaller diameter, permitting a further profound treatment of the root canal.

The present invention relates to root canal instrument sets for the crown-down preparation.

Root canal instrument sets of the above-mentioned type are described in DE 101 35 820 C1 or DE 101 35 821 C1.

Like the root canal instrument sets known from the above-mentioned prior art, the root canal instrument set according to the invention serves for a mechanical root canal treatment. It is here particularly important that the individual root canal instruments are optimized with respect to their loadability and breakage safety. The cutting geometry also plays an important role in this context. Furthermore, it must be ensured that an adequate chip chamber is provided for removal of the material.

It is the object of the present invention to provide a root canal instrument set of the above-indicated type which ensures a high degree of breakage safety together with optimum chip removal and optimum working conditions.

According to the invention, this object is achieved by the feature combination of the main claim; the subclaims show further advantageous developments of the invention.

According to the invention, a first root canal instrument is thus provided on its working part with four cutting edges and a root canal instrument to be used there-after is provided on its working part with five cutting edges.

The root canal instrument set according to the invention is characterized by a number of considerable advantages. The different numbers of cutting edges yield cutting geometries varying from root canal instrument to root canal instrument. Thus, the first-mentioned root canal instrument with four cutting edges has a large cross-section which ensures breakage safety and strength while an adequately large chip chamber is available when four cutting edges are used.

In the subsequent instrument, which due to the crown-down preparation technique has a smaller diameter, five cutting edges are provided according to the invention, said five cutting edges offering a maximum degree of cross-sectional area. This provides for both high loadability and high breakage safety. An adequately large chip chamber is still provided for removing the material arising in the subsequent treatment process.

The cross-sectional shape can be configured according to the invention such that in the case of four cutting edges it forms a square cross-sectional area or that a symmetrical cross-sectional shape is obtained. This may e.g. be a rhombic configuration. The cross-section has two identical edge angles arranged opposite each other.

The cross section of the root canal instrument provided with five cutting edges may be configured in the form of a regular pentagon. However, it is also possible to choose an irregular symmetrical structure in which e.g. two opposite identical edge angles are provided.

The configuration of the root canal instruments of the root canal instrument set according to the invention thus effects enhanced breakage safety and mechanical loadability in comparison with the prior art. Chips are removed in an optimum manner at the same time. The selected edge angles, which also define the cutting geometry, accomplish a high cutting ease in the root canal instruments.

According to the invention, it is possible to give the root canal instruments a different twist, e.g. a constant twist, a dynamic twist or a twist of a variable kind.

According to the invention, the working parts of the root canal instrument may be provided either with a ball-shaped outer contour or with a conical outer contour.

In response to the respective conditions of use, the root canal instrument set according to the invention may comprise two, three, four or more root canal instruments. When three or four root canal instruments are used in the root canal instrument set of the invention, it is possible that the first two root canal instruments to be used have four cutting edges while the third root canal instrument or the fourth root canal instrument is provided with five cutting edges.

A root canal instrument set according to the invention with four root canal instruments could e.g. be configured as follows:

Root Canal Instrument 1:
Working length (neck and working part): 19 mm
Ball-shaped working parts with a rough taper of 08 to 12
Working part length: 8 to 12 mm Root Canal Instrument 2:
Working length (neck and working part): 22 mm
Ball-shaped working parts with a rough taper of 06 to 08
Working part length: 8 to 12 mm Root Canal Instrument 3:
Working length (neck and working part): 25 mm
Ball-shaped working parts with a rough taper of 04 to 06
Working part length: 8 to 12 mm Root Canal Instrument 4:
Working length (neck and working part): 25 mm
Ball-shaped working parts with a rough taper of 02 to 04
Working part length: 8 to 12 mm The taper that is possible in the configuration of the cutting edges is indicative of the conicity. A numerical value of e.g. 04 indicates that the conicity of the working part over a length of 1 mm of the working part changes by 0.04 mm in diameter.

The invention shall now be described with reference to embodiments in combination with the drawing, in which.

Figure 1:
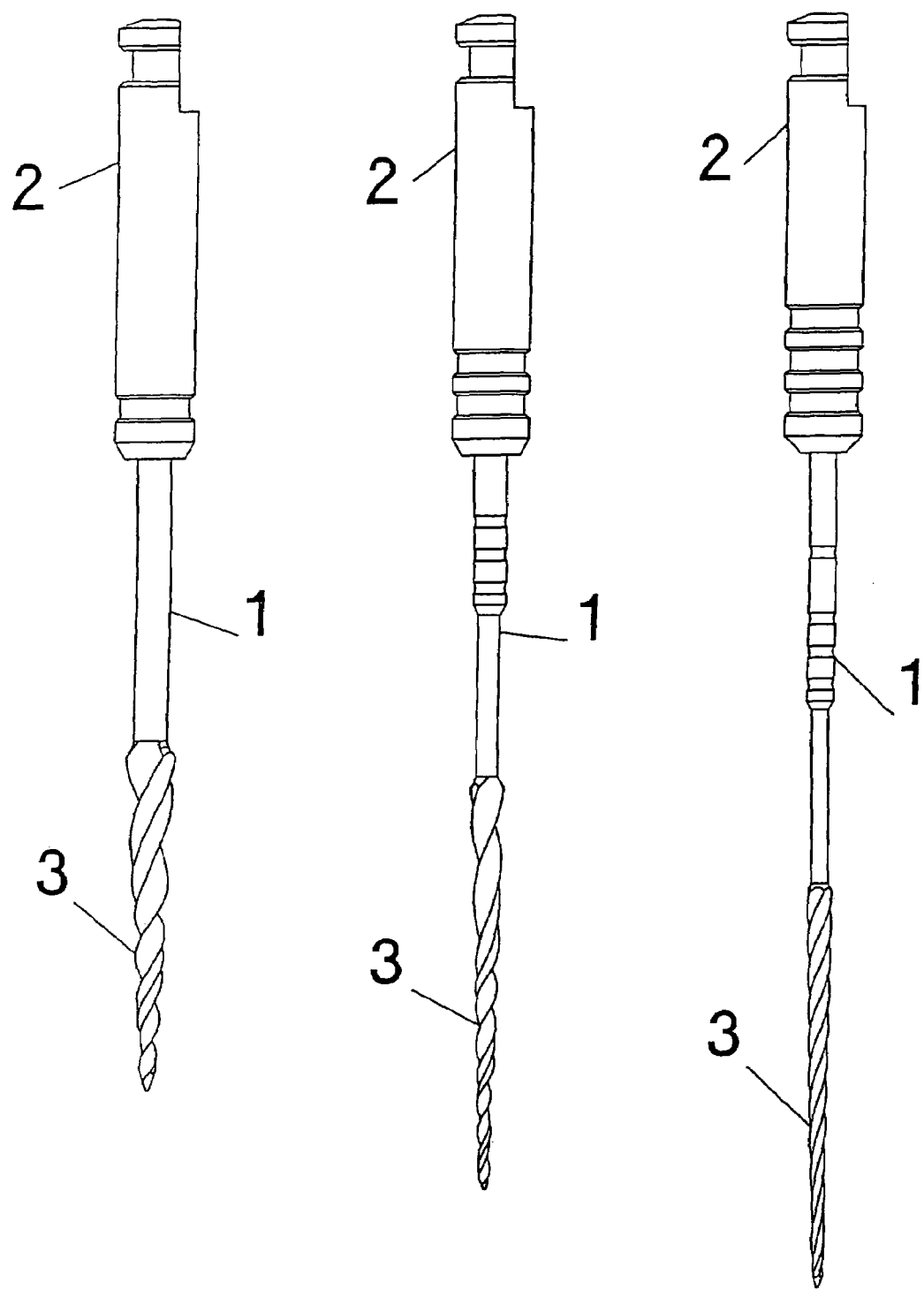
FIG. 1 is a schematic illustration of a root canal instrument set according to the invention with three root canal instruments.

FIG. 1 is a schematic illustration showing a root canal instrument set including three root canal instruments to be used one after the other. The number of the grooves in the shaft is indicative of the sequence. The root canal instrument comprises a neck 1 the free end of which is provided with a working part 3. In the illustrated embodiment, said working part is ball-shaped with respect to its envelope. At the other end of the neck, a shaft end 2 is provided which is configured such that the root canal instrument can be inserted into a drive mechanism to carry out a mechanical root canal treatment.

Each of FIGS. 2 to 5 is a sectional view taken through the working part 3. The circle describes the circumferential envelope on which the respective cutting edges 4 are arranged that are formed by the edges of the cross-sectional profile. According to FIG. 2, a square cross-sectional shape is provided in which identical edge angles of 90° are obtained.

Figure 3:
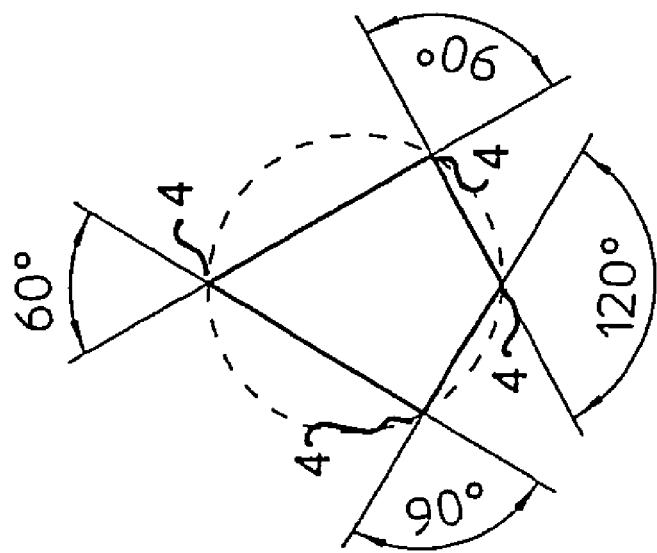
FIG. 3 is an alternative configuration with four cutting edges by analogy with FIG. 2.
Figure 2:
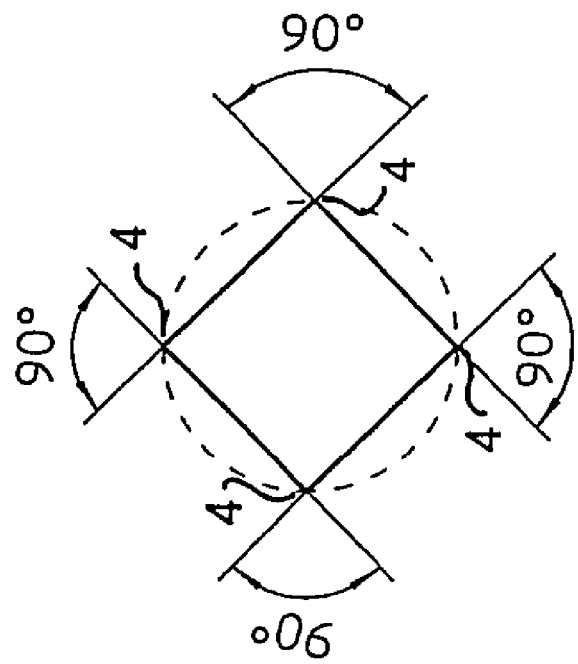
FIG. 2 is a sectional view through a working part of a root canal instrument with four cutting edges.

FIG. 3 is a cross-sectional shape in the form of an irregular rhombus. Two opposite edge angles of 90° are provided, whereas the two other edges angles are 60° and 120°, respectively. It follows from the illustration of FIG. 3 that different cutting geometries are particularly defined by the different edge angles. The edge angle corresponds to the wedge angle according to the definitions of the cutting geometry of a cutting tool.

Figure 4:
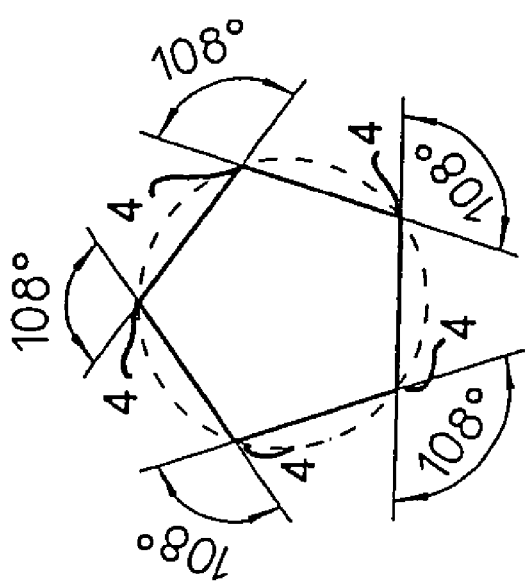
FIG. 4 is a sectional view of a root canal instrument with five cutting edges.

FIG. 4 shows a cross-sectional shape with five cutting edges configured in the shape of a regular pentagon with edge angles of 108° each.

Figure 5:
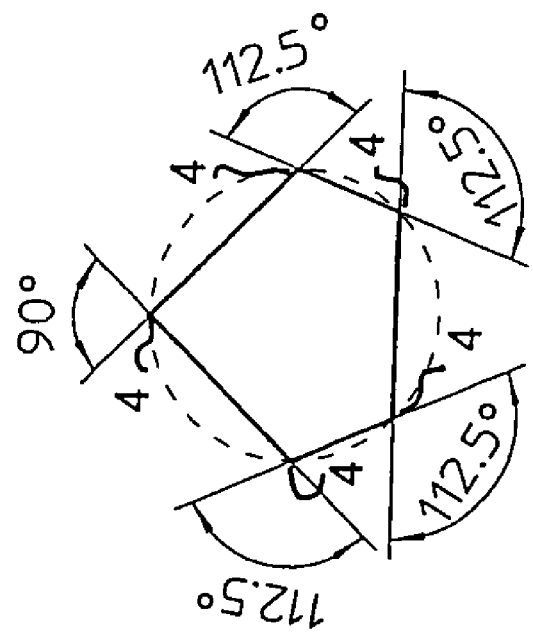
FIG. 5 is an alternative configuration of a cross section with five cutting edges.

The embodiment shown in FIG. 5 yields the shape of an irregular pentagon, four of the edge angles being identical.

Thus, the cross-sectional shapes of FIGS. 3 and 5 are each in symmetry with a symmetrical line arranged perpendicular to the rotational axis (not shown) of the root canal instrument.

The invention claimed is:

1. A root canal instrument set comprising at least two root canal instruments, each root canal instrument having (i) a shaft positioned at one end thereof; (ii) a working part having at least one cutting edge positioned at an opposite end thereof; and (iii) a neck position between said shaft and said working part, wherein one of said root canal instruments has a larger diameter than another of said root canal instruments;

wherein a first root canal instrument of said set has four cutting edges on its corresponding working part, and another of said root canal instruments has five cutting edges on its corresponding working part; and wherein said root canal instrument having four cutting edges further has a cross-sectional shape in the form of an irregular rhombus and said root canal instrument having five cutting edges has a symmetrical cross-section forming a pentagon.

2. The root canal instrument set of claim 1, wherein the root canal instrument having five cutting edges is shaped in the form of an irregular pentagon, wherein four edge angles are identical.

3. The root canal instrument set of one of claim 1, wherein at least one cross-section has two identical edge angles opposite one another.

4. The root canal instrument set of claim 1, wherein the root canal instrument set comprises two root canal instruments.

5. The root canal instrument set of claim 1, wherein the root canal instrument set comprises three root canal instruments.

6. The root canal instrument set of claim 1, wherein the root canal instrument set comprises four root canal instruments.

7. The root canal instrument set of claim 1, wherein the root canal instruments are dimensioned according to a crown-down-principle.

8. The root canal instrument set of claim 1, wherein the root canal instruments have a curved outer contour at their respective working parts.

* * * * *